US012527911B2

(12) United States Patent
Pierquin et al.

(10) Patent No.: US 12,527,911 B2
(45) Date of Patent: Jan. 20, 2026

(54) DEVICE FOR INJECTING A PRODUCT

(71) Applicant: Nemera La Verpillière, La Verpilliere (FR)

(72) Inventors: Thibaut Pierquin, Caluire et Cuire (FR); Sébastien Diet, Les Houches (FR); Pierre Pintus, Crachier (FR); Gaëtan Grenot, Lyons (FR); Sébastien Delvalac, Lyons (FR); Marc Todesco, Tignieu-Jameyzieu (FR)

(73) Assignee: Nemera La Verpilliere, Le Verpilliere (FR)

( * ) Notice: Subject to any disclaimer, the term of this patent is extended or adjusted under 35 U.S.C. 154(b) by 789 days.

(21) Appl. No.: 17/780,343

(22) PCT Filed: Nov. 26, 2020

(86) PCT No.: PCT/EP2020/084528
§ 371 (c)(1),
(2) Date: May 26, 2022

(87) PCT Pub. No.: WO2021/105520
PCT Pub. Date: Jun. 3, 2021

(65) Prior Publication Data
US 2023/0001085 A1 Jan. 5, 2023

(30) Foreign Application Priority Data
Nov. 26, 2019 (FR) ....................................... 1913273

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 2005/14252* (2013.01); *A61M 2005/1585* (2013.01)

(58) Field of Classification Search
CPC .............. A61M 5/158; A61M 5/14248; A61M 2005/14252; A61M 2005/1585
See application file for complete search history.

(56) References Cited

U.S. PATENT DOCUMENTS

2016/0089491 A1* 3/2016 Smith ................ A61M 5/1452 604/154
2018/0021508 A1* 1/2018 Destefano ......... A61M 5/14248 604/151
(Continued)

FOREIGN PATENT DOCUMENTS

WO 2015032745 A1 3/2015
WO 2015164645 A1 10/2015
(Continued)

*Primary Examiner* — James D Ponton
(74) *Attorney, Agent, or Firm* — Farber LLC

(57) ABSTRACT

A device for injecting a product into a site, having:
- a body provided with a bearing wall for bearing on the site,
- a needle support mounted so as to be movable with respect to the bearing wall between:
- a pre-insertion position,
- at least one insertion position, and
- at least one retracted position,
- a catheter mounted so as to be movable with respect to the needle and intended to dispense product into the site,
- a drive unit intended to translate the needle support between the various positions of the needle support,
- a pump connected to a reservoir so as to transfer product from the reservoir to the catheter,
- a single electric motor intended to drive the drive unit and to supply the pump.

19 Claims, 3 Drawing Sheets

(56) References Cited

U.S. PATENT DOCUMENTS

| | | | | |
|---|---|---|---|---|
| 2019/0015582 | A1 | 1/2019 | Naftalovitz et al. | |
| 2019/0209773 | A1* | 7/2019 | Shor | H03H 9/64 |
| 2019/0365993 | A1* | 12/2019 | Staub | A61M 5/3287 |

FOREIGN PATENT DOCUMENTS

| | | | |
|---|---|---|---|
| WO | 2016041872 | A1 | 3/2016 |
| WO | 2018060027 | A1 | 4/2018 |
| WO | 2018219842 | A1 | 12/2018 |
| WO | 2019036181 | A1 | 9/2019 |

* cited by examiner

DEVICE FOR INJECTING A PRODUCT

FIELD OF THE INVENTION

The invention relates to a device for injecting a product into a site. The invention relates more particularly to a device for inserting a needle used to dispense a product into the site where the needle was inserted, especially by using a catheter (or cannula).

BACKGROUND OF THE INVENTION

The state of the art, in particular document WO2015164645, already describes a device for inserting a needle in order to insert a catheter (or cannula) to dispense a medication. The device comprises a torsion spring allowing a movement in vertical translation of a needle support when the spring changes from a compressed state to a relaxed state. The device further comprises a pump system, independent of the torsion spring, allowing the medication to be dispensed from a reservoir. In addition, the use of a spring or any other preset drive element in this type of device causes a certain amount of wear of the plastic parts with which it interacts. Due to the robustness required to prevent any accidental activation, this use may also cause assembly and/or operating difficulties, for example regarding reproducibility of the movements.

SUMMARY OF THE INVENTION

A connection element must in fact firstly be assembled with the needle support, then the assembly is attached to the base while taking care to compress the torsion spring against a stop provided on the base and to insert a drive pin in a camway. This implies various assembly constraints. In addition, insertion of the needle and dispensing of the medication are controlled independently, which means that the insertion device requires more components and is therefore larger.

The invention aims in particular to overcome the above-mentioned disadvantages and to provide a more compact injection device that is easier to assemble.

The invention therefore relates to a device for injecting a product into a site comprising:

- a body provided with a bearing wall for bearing on the site,
- a needle support on which a needle is mounted, the needle support being mounted so as to be movable with respect to the bearing wall between:
  - a pre-insertion position in which the needle is retracted with respect to the bearing wall,
  - at least one insertion position in which the needle protrudes with respect to the bearing wall, and
  - at least one retracted position in which the needle is once again retracted with respect to the bearing wall,
- a catheter mounted so as to be movable with respect to the needle and intended to dispense product into the site,
- a drive unit intended to translate the needle support between the various positions of the needle support,
- a pump connected to a reservoir so as to transfer product from the reservoir to the catheter,
- a single electric motor intended to drive the drive unit and for supplying the pump to transfer the product.

The injection device as proposed by this invention requires a single motor which inserts the needle and injects product, which reduces the size of the injection device and the manufacturing cost. Assembly is therefore easier since there are fewer parts. In particular, there is no need to provide for a specific return unit to actuate the needle insertion, which reduces the number of parts subject to wear. Moreover, control of the needle and catheter insertion movement is more precise and easier thanks to the drive by the electric motor.

According to other optional characteristics of the injection device taken alone or in combination:

- The electric motor is configured to:
  - rotate in a first direction of rotation so that the drive unit drive the needle support towards the at least one insertion position;
  - rotate in a second direction of rotation so that the pump operates in order to transfer product from the reservoir to the catheter, and preferably so that the drive unit drive the needle support towards the at least one retracted position, preferably simultaneously.

Thus, the various functions performed by the single electric motor take place simply by changing the direction of rotation of the electric motor, which is easy to control. It is understood that the second direction of rotation corresponds to a direction of rotation opposite to the first direction of rotation. Since the needle is retracted and the product dispensed at the same time, the injection device is even more efficient.

- The drive unit comprises a series of teeth arranged on the circumference of a rotating element of the electric motor and intended to cooperate with a rack carried by at least the needle support or a complementary drive element preferably configured to be connected in translation with the needle support.

Since the teeth cooperate with the rack, rotation of the rotating element is easily converted into translation of the needle support, more particularly when inserting and retracting the needle.

It is understood that the rack can be carried exclusively by the needle support (for example the complementary drive element and the needle support are made in one piece), which means that one part less is required. The complementary drive element may also consist of a part separate from the needle support, in which case the use of such a complementary drive element, which is in direct contact with the rotating element, means that the needle support can take different shapes to meet any constraints relating to the arrangement or size of the injection device. Lastly, the needle support and the complementary drive element may simultaneously include surfaces forming the rack so that the movements of these elements in the injection device are controlled more precisely.

- The injection device comprises a catheter support adapted to move the catheter with the needle when the needle support changes from its pre-insertion position to the at least one insertion position and to separate it from the needle so that its movement remains locked when the needle support changes from its insertion position to the at least one retracted position.
- The injection device comprises a locking member configured to cooperate with notches carried by the catheter support in order to lock the movement of the catheter support and define at least first and second needle support insertion positions.

The locking member and the notches lock the movement of the catheter support with respect to the bearing wall in at least two different positions corresponding to at least two different insertion positions of the needle support. It is particularly interesting to be able to vary the needle support insertion positions in order to vary the product injection depth and thus adapt the injection to variables such as the user's morphology or the type of injection required.

The catheter support and the complementary drive element are configured to be:

connected in translation when moving the needle support from its pre-insertion position to the at least one insertion position, and movable with respect to each other when moving the needle support from the at least one insertion position to the at least one retracted position.

The injection device comprises an elastic element carried by the catheter support or the complementary drive element, the elastic element being configured to keep the complementary drive element in contact with the drive unit when the electric motor rotates in the second direction of rotation before inserting the needle.

By using such an elastic element, it is possible to use a priming function which purges the air present in the reservoir or upstream from the catheter, so as to bring product into the catheter. When the motor rotates in the second direction of rotation, in fact, during normal operation (excluding priming), the drive unit drive the needle support towards the at least one retracted position with respect to the catheter support.

The elastic element can be used to attach the rack to the catheter support during priming, before inserting the needle and the catheter into the body of the subject. Similarly, the elastic element provides an additional and indirect attachment link between the catheter support and the needle support.

With this ingenious configuration, a single motor is required to insert the needle, transfer product and prime the device.

Advantageously, a stop interacts with the elastic element so that the rack continues to interact with the drive unit. The elastic element and the stop no longer interact when the rack and the needle support are retracted after insertion. Advantageously, the elastic element can also be used to hold the assembly (rack, catheter support and needle support) together during the steps of handling the injection device (storage, transport and priming phase).

The injection device comprises a base having a guide housing defining a guide axis and intended to receive a needle support, and in which the needle support comprises blocking member configured to cooperate with complementary blocking member carried by the guide housing when the needle support is in the pre-insertion position and in the at least one retracted position.

The blocking member and the complementary blocking member hold the needle during injection and guarantee the stability of the needle when the needle support is stationary, i.e. before inserting (including during priming) and after inserting the catheter.

The complementary drive element is configured to be connected in translation with the needle support only when moving the needle support from its pre-insertion position to the at least one insertion position, and from the at least one insertion position to the at least one retracted position, the complementary drive element being movable with respect to the needle support when the needle support is in the pre-insertion position or in the at least one retracted position.

This allows the drive unit to rotate during priming and injection, the movement of the complementary drive element therefore not being hindered by the needle support.

The complementary drive element comprises a flexible portion carrying the rack, the flexible portion preferably having an arcuate shape.

Due to this architecture and shape, the complementary drive element can be arranged horizontally before and after inserting the needle in order to further reduce the size of the injection device.

The drive unit comprises a first series of teeth arranged on the circumference of a rotating element and intended to cooperate with a second series of teeth carried by a complementary rotating element provided with a camway configured to guide the needle support in translation.

This arrangement reduces the size of the injection device.

The invention also relates to a kit for assembling a device for injecting a product into a site comprising:

a body provided with a bearing wall for bearing on the site, a needle support, the needle support being mounted so as to be movable with respect to the bearing wall between:

a pre-insertion position in which the needle is retracted with respect to the bearing wall, at least one insertion position in which the needle protrudes with respect to the bearing wall, and at least one retracted position in which the needle is once again retracted with respect to the bearing wall, a catheter configured so as to be movable with respect to the needle and intended to dispense product into the site, a drive unit intended to translate the needle support between the various positions of the needle support, a pump connected to a reservoir so as to transfer product from the reservoir to the catheter, a single electric motor intended to drive the drive unit and for supplying the pump to transfer the product.

BRIEF DESCRIPTION OF THE DRAWINGS

The invention will be better understood on reading the following description, given solely by way of example and with reference to the accompanying drawings in which.

DETAILED DESCRIPTION OF THE INVENTION

FIG. 1 and FIG. 4*a* through 4*e* show an injection device according to one embodiment of the invention, designated by the general reference 1. As shown on FIG. 1, the injection device 1 comprises a body 2 having a bearing wall 19 intended to be placed in direct contact with the skin of a patient. The injection device 1 is configured to inject a product, preferably liquid, generally a medication, into a site of the patient for a relatively long duration, generally several minutes, or even several hours.

The pharmaceutical products likely to be used in the insertion device include for example peptides, proteins, hormones, active substances of biological origin, nucleotide-based active substances, nutritional formulae and other substances.

These active substances may include, but are not limited to, insulins, insulin analogues such as insulin lispro or insulin glargine, insulin derivatives, C-peptide, GLP-1 receptor agonists such as dulaglutide or liraglutide, glucagon, glucagon analogues, glucagon derivatives, gastric inhibitor polypeptides (GIP), GIP analogues, GIP derivatives, oxyntomodulin analogues, oxyntomodulin derivatives, therapeutic antibodies, such as monoclonal antibodies and any therapeutic agent that can be delivered by the above device. The medication as it is used in the device can be formulated with one or more excipients.

The injection device 1 can therefore be carried by the user during the injection, for example on the waist.

Figure 1:
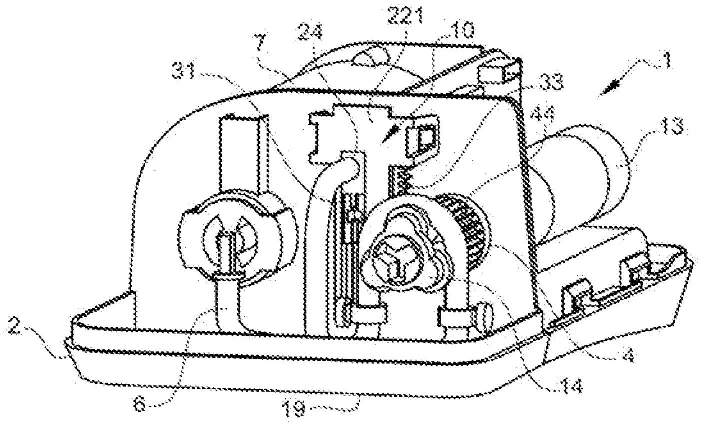
FIG. 1 is a partial perspective view of an injection device according to one embodiment of the invention.

The injection device 1 further comprises, as shown again on FIG. 1, an electric motor 13 comprising a shaft fitted with a drive unit 4, 44 which consist, in the example shown, in a rotating element 4 provided with a series of teeth 44 distributed uniformly on the circumference of the rotating element 4. The electric motor 13 can rotate in a first direction of rotation S1 (see FIG. 3*c* for example) and a second direction of rotation S2 (see FIG. 3*d* for example).

The injection device 1 also comprises a pump 14, for example a peristaltic pump as shown on FIG. 1, mounted coaxially with the rotating element 4 and actuated by the same electric motor 13. The pump 14 is connected to a reservoir 7 of product by means of a flexible tube 6 so that when the pump 14 is operated, product is transferred from the reservoir 7 to an injection unit 10 which will be described below. FIG. 1 is a partial view of the injection device 1 since the latter may comprise a lid or box forming a closed space with the bearing wall 19 so that the elements described previously cannot be seen or accessed from the outside of the injection device 1.

Figure 2:
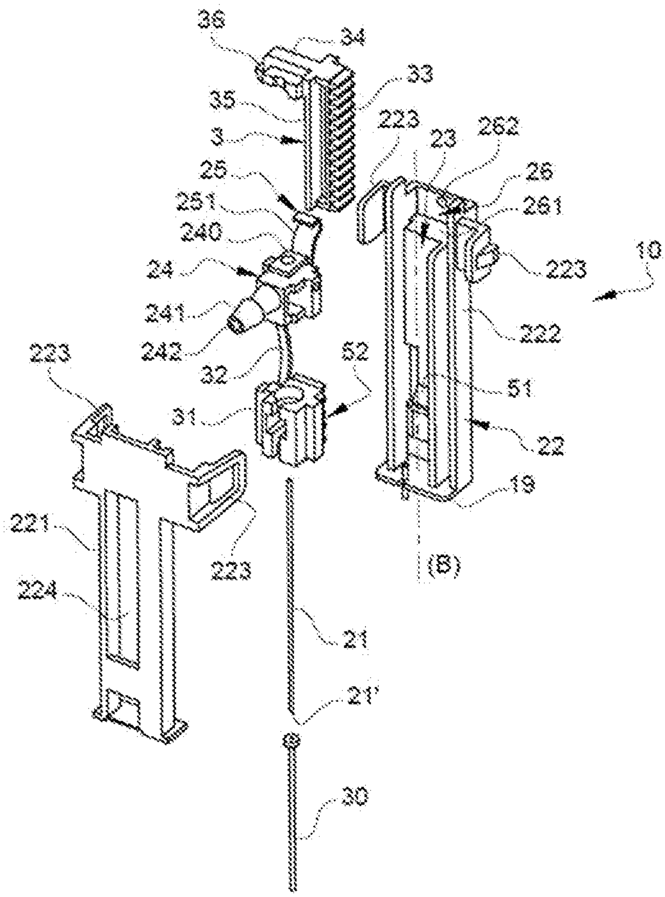
FIG. 2 is an exploded view of a sub-assembly of the injection device of FIG. 1.

FIG. 2 shows a sub-assembly of the injection device 1, which is an injection unit 10. The injection unit 10 comprises a base 22 comprising a first vertical guide 221 and a second vertical guide 222 forming a guide housing 23 defining a guide axis (B). The first vertical guide 221 and the second vertical guide 222 are fixedly mounted to each other, by clipping member 223 for example. The guide axis (B) can be designed to be substantially perpendicular to the bearing wall 19 or according to any other suitable inclination. In addition, the base 22 comprises, on the first vertical guide 221, a through opening 224 having a longitudinal shape along the guide axis (B). The base 22 also comprises a locking member 51 carried by the second vertical guide 222 near the bearing wall 19. The functions of the various elements carried by the base 22 are described below.

As shown on FIG. 2, the injection unit 10 comprises a needle support 24 mounted so as to be movable in the guide housing 23 between various positions as shown on FIG. 3*a* through FIG. 3*e* and FIG. 4*a* through FIG. 4*e*. The needle support 24 comprises a main block 240 of substantially cross-shaped section along a plane parallel to the bearing wall 19. In addition, the shape of the main block 240 is substantially complementary to that of the guide housing 23, so that the needle support 24 can slide in the guide housing 23 along the guide axis (B).

The needle support 24 further comprises a blocking member 25, consisting of an elastic hook 251 mounted on a flexible portion, the blocking member 25 being configured to cooperate with complementary blocking member 26 comprising a first vertical stop 261 and a second vertical stop 262 carried by the base 22, the cooperation between the blocking member 25 and the complementary blocking member 26 being shown more clearly on FIG. 4*a* through FIG. 4*e*.

As shown on FIG. 2 and FIG. 4*a* through 4*e*, the needle support 24 also comprises a protuberance 241 intended to cross the longitudinal through opening 224 and to slide therein. The protuberance 241 is intended to be connected to the tube 6 as shown on FIG. 1 to allow fluid communication with the reservoir 7 and the product it contains. To do this, the protuberance 241 is provided with a dispensing channel 242 as shown on FIG. 4 to transfer product into the needle support 24. An insertion needle 21 is fixedly mounted to the needle support 24 and is provided with a lateral orifice in fluid communication with the dispensing channel 242, thus allowing the product to be injected to reach the insertion end 21' and therefore the injection site once the needle 21 has been inserted.

According to the invention, the needle support 24 is mounted so as to be movable with respect to the bearing wall 19 between:

- a pre-insertion position in which the needle 21 is retracted with respect to the bearing wall 19,
- at least one insertion position in which the needle 21 protrudes with respect to the bearing wall 19, and
- at least one retracted position in which the needle 21 is once again retracted with respect to the bearing wall 19.

To do this, the injection unit 10 comprises a complementary drive element 3 (see FIG. 2 for example) intended to translate the needle support 24 between the various positions of the needle support 24. As shown on FIG. 2 and FIG. 4*a* through 4*e*, the complementary drive element 3 is L-shaped and comprises a first horizontal portion 34 which extends along an axis perpendicular to the guide axis (B), and a second vertical portion 35 which extends along an axis parallel to the guide axis (B). The first portion 34 has a flat surface as shown on FIG. 4*a* through 4*e* intended to come into contact with the needle support 24 and to move the needle support 24. The first portion 34 further comprises a locking pin 36 (see FIG. 3*a* for example) arranged at one end of the first portion 34 opposite the second portion 35. The second portion 35 is provided with a rack 33 (see FIG. 2 for example) intended to cooperate with the series of teeth 44 on the rotating element 4 so that the complementary drive element 3 can be driven in translation along the guide axis (B) in the two directions opposite to each other and according to the first and second directions of rotation S1, S2 of the electric motor 13.

The injection unit 10 also comprises a catheter 30 carried by a catheter support 31, as shown on FIG. 2 and FIG. 4*a* through 4*e*. In the example shown, in particular on FIG. 2 and FIG. 3*a* through FIG. 3*e*, the catheter support 31 comprises an arcuate-shaped elastic element 32, having one end attached to the catheter support 31 and the other end forming a stop intended to cooperate with the locking pin 36 so that the rack 33 continues to interact with the series of teeth 44. Advantageously, the elastic element 32 and the locking pin 36 no longer interact when the rack 33 and the needle support 24 are retracted after insertion of the needle 21 and rotation of the electric motor 13 according to a second direction of rotation S2 (see FIG. 3*d* and FIG. 3*e*).

The catheter support 31 is connected in translation to the needle support 24 during insertion of the needle 21. The catheter 30 is movably mounted with respect to the needle 21. Similarly, since the needle 21 is housed inside the catheter 30, insertion of the needle 21 into the site allows simultaneous insertion of the catheter 30.

Figure 3A:
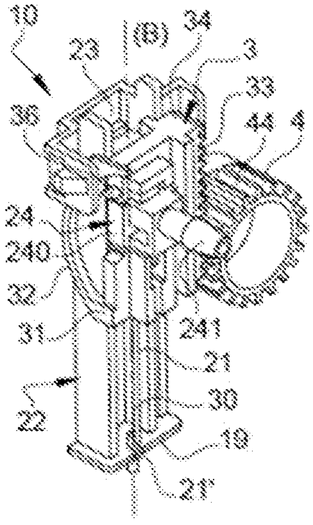
FIG. 3*a* through FIG. 3*e* are a set of perspective views illustrating various operating steps of the sub-assembly of the injection device of FIG. 2 interacting with drive unit.
Figure 3B:
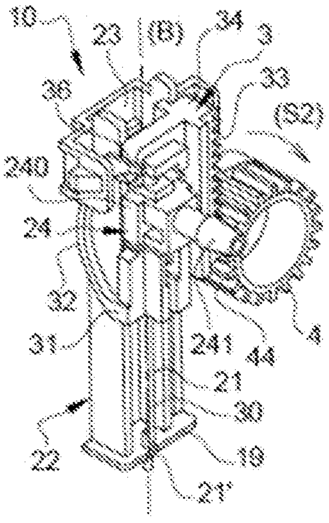
Figure 3C:
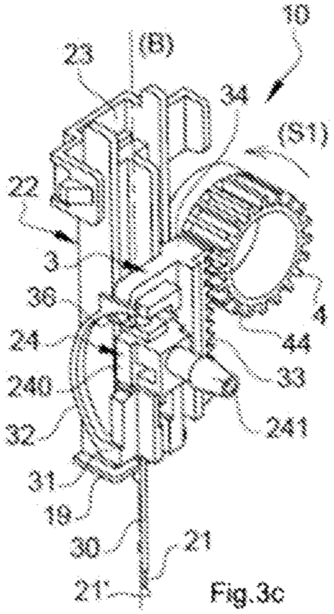
Figure 3D:
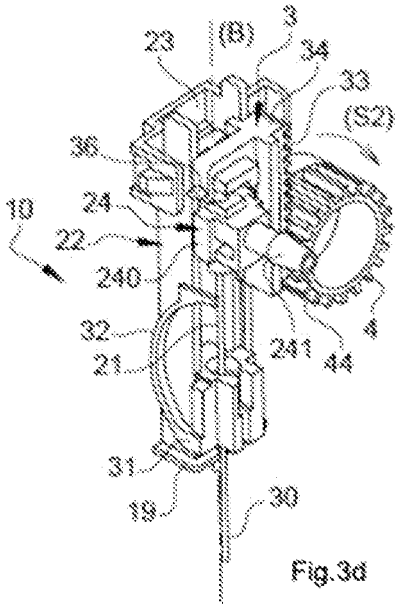
Figure 3E:
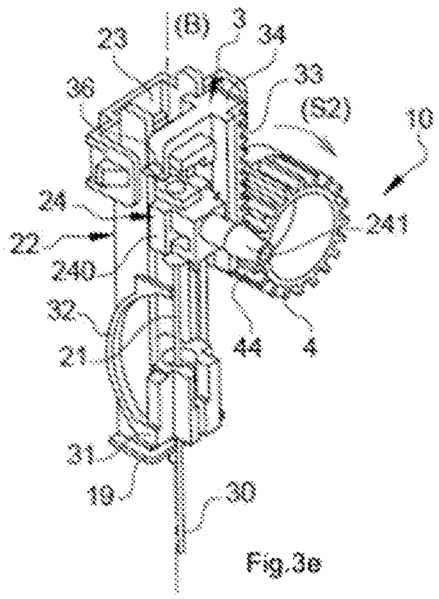
Figure 4A:
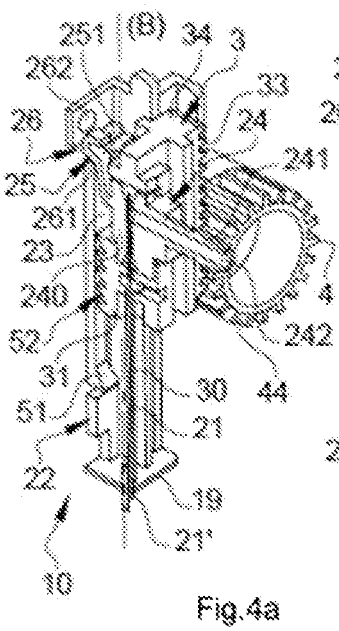
FIG. 4*a* through FIG. 4*e* are a set of cross-sectional and perspective views illustrating the operating steps of the sub-assembly of the injection device of FIGS. 3*a*-3*e*.
Figure 4B:
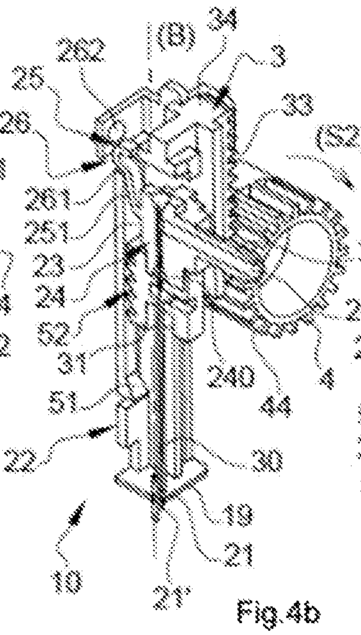

FIG. 3*a* through FIG. 3*e* and FIG. 4*a* through FIG. 4*e* show the various operating steps of the injection device 1, which will be described as follows: when the injection device 1 is ready to be used by a patient or by a member of the medical staff, the needle support 24 is in a pre-insertion position in which the needle 21 is retracted with respect to the bearing wall 19. The needle support 21 is kept in this pre-insertion position by the interaction between the blocking member 25, in this case consisting of an elastic hook 251 and the complementary blocking member 26 (FIG. 3*a* and FIG. 4*a*). The catheter support 31 and the complementary drive element 3 are also kept in this pre-insertion position since they are respectively against the needle support 21 on one side and blocked in translation by the interaction between the elastic element 32 and the locking pin 36 carried by the complementary drive element 3 on the other side.

When the user places the injection device 1 on a site to be injected, the bearing wall 19 is for example in direct contact with the site. The user then activates the electric motor 13, using a control button for example, to rotate the electric motor 13 as well as the rotating element 4 in the second direction of rotation S2 as shown on FIG. 3*b* and FIG. 4*b*. The injection device 1 is then in priming phase, during which the pump 14 starts to transfer product from the reservoir towards the catheter 30, successively via the tube 6, the pump 13 and the needle 21. This priming phase is programmed to last for a short period of time, but sufficient to purge the air present upstream from the catheter 30.

During the priming phase, the series of teeth 44 carried by the rotating element 4 in contact with the rack 33 carried by the complementary drive element 3 drives the latter in an upward direction with respect to the guide axis (B), i.e. in a direction away from the bearing wall 19. Simultaneously, the elastic element 32 presses down on the pin 36, i.e. in a downward direction with respect to the guide axis (B) and therefore towards the bearing wall 19.

Thus, the complementary drive element 3 exerts a very small back and forth movement so that the complementary drive element 3 continues to interact with the series of teeth 44 of the rotating element 4. The complementary drive element 3 is therefore brought into contact with the drive exerted by the rotation of the rotating element 4 in the second direction of rotation S2 and can therefore continue priming the injection device 1.

When priming of the injection device 1 is finished, the electric motor 13 rotates in a first direction of rotation S1, which is opposite to the second direction of rotation S2, to drive the needle support 24 towards a preset insertion position. More precisely, the series of teeth 44 engages with the rack 33 and converts the rotation of the rotating element 4 into translation of the complementary drive element 3 towards the bearing wall 19. The complementary drive element 3 itself drives the needle support 24 and the catheter support 31 in the same direction towards the bearing wall 19 as shown on FIGS. 3*c* and 4*c*. When the needle support 24 leaves its pre-insertion position and moves towards the bearing wall 19, the blocking member 25 then no longer interact with the complementary blocking member 26, since the blocking member 25 comprise an elastic hook 251 which is held completely inside the guide housing 23 as shown on FIG. 4*c*.

Figure 4C:
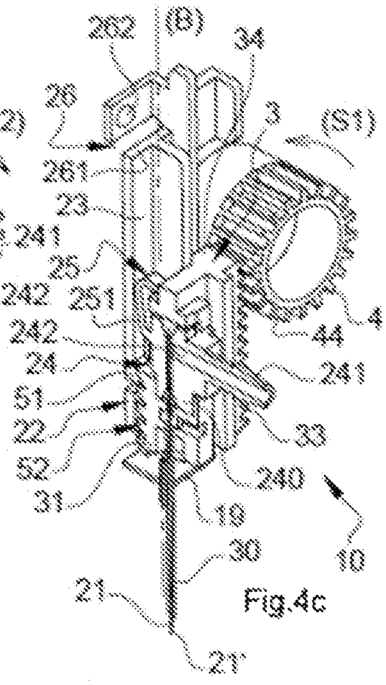
Figure 4D:
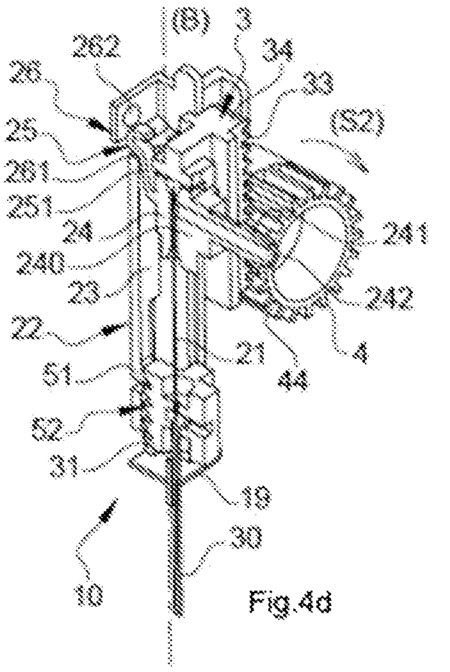
Figure 4E:
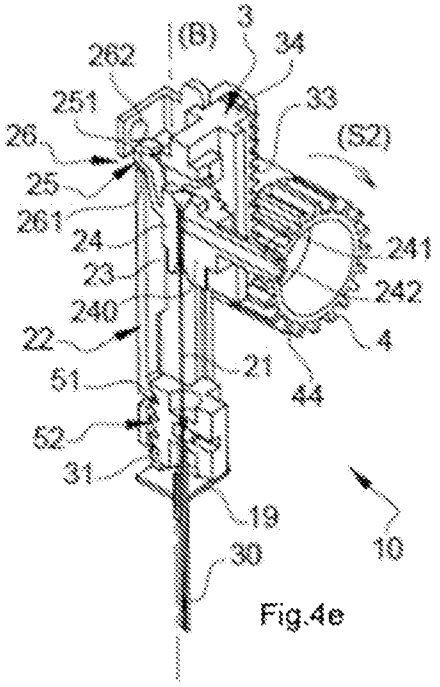

When the needle support 24 has nearly reached the bearing wall 19, the notches 52 carried by the catheter support 31 start to come into contact with the locking member 51, one after the other. If the needle support 24 reaches the preset insertion position, the corresponding notch which is already in contact with the locking member 51 continues to cooperate with the locking member 51 to keep the catheter support 31 in position. If the needle support 24 has not reached the preset insertion position, the rack 33 continues to move until the needle support 24 reaches the preset insertion position. FIG. 4*c* through 4*e* show an insertion position in which the last notch which comes into contact with the locking member 51 cooperates with the latter to keep the catheter support 31 in a position which corresponds to a "shallow" insertion position of the needle 21, equivalent for example to the subcutaneous layer of the patient's skin. According to the example shown, the needle support 24 can have up to 5 different insertion positions.

Once the catheter 30 has been inserted into the site by inserting the needle 21, the needle support 24 separates from the catheter support 31 and moves from its insertion position to its retracted position. To do this, the electric motor 13 rotates again in the second direction of rotation S2 so that the drive unit 4, 44 drive the complementary drive element 3 and the needle support 24 in an upward direction with respect to the guide axis (B), towards the retracted position of the needle support 24. Since the driving force of the electric motor 13 is greater than the clipping between the notches 52 and the locking member 51, the elastic element 32 and the locking pin 36 no longer cooperate and the complementary drive element 3 separates from the catheter support 31. The needle support 24 is connected in translation with the complementary drive element 3 by the hooking formed by the blocking member 25 via the elastic hook 251 on the first horizontal portion 34 of the complementary drive element 3.

As the needle 21 is being removed, the electric motor 13 rotates in the second direction of rotation S2 and therefore operates the pump 14 in order to transfer a preset quantity of product from the reservoir 7 to the catheter 30.

When the needle support 24 reaches the retracted position, the elastic hook 251 and the complementary blocking member 26 cooperate again to lock the needle support 24 in this retracted position, as shown on FIGS. 3*d* and 4*d*. Since the elastic hook 251 is no longer in contact with the first horizontal portion 34 of the complementary drive element 3, the latter becomes movable with respect to the needle support 24. The needle support 24 is then stable in the retracted position where it is held. Thus, the electric motor 13 can continue to rotate in the second direction of rotation S2 in order to finalise the transfer of the preset quantity of product.

The injection device 1 is for example assembled using an assembly kit comprising:

- a body 2 provided with a bearing wall 19 for bearing on the site,
- a needle support 24, the needle support 24 being mounted so as to be movable with respect to the bearing wall 19 between:
  - a pre-insertion position in which the needle 21 is retracted with respect to the bearing wall 19,
  - at least one insertion position in which the needle 21 protrudes with respect to the bearing wall 19, and
  - at least one retracted position in which the needle 21 is once again retracted with respect to the bearing wall 19,
- a catheter 30 configured so as to be movable with respect to the needle 21 and intended to dispense product into the site,
- a drive unit 4, 44 intended to translate the needle support 24 between the various positions of the needle support 24, a pump 14 connected to a reservoir so as to transfer product from the reservoir to the catheter 30, a single electric motor 13 intended to drive the drive unit 4, 44 and for supplying the pump 14 to transfer the product.

The invention is not limited to the embodiments described and other embodiments will be clearly apparent to those skilled in the art.

The complementary drive element 3 may in particular comprise a flexible portion carrying the flexible rack 33, the flexible portion preferably having an arcuate shape.

The drive unit could also comprise a first series of teeth arranged on the circumference of a rotating element and intended to cooperate with a second series of teeth carried by a complementary rotating element provided with a camway configured to guide the needle support 24 in translation.

The invention claimed is:

1. An injection device for injecting a product into a site, comprising:

a body provided with a bearing wall for bearing on the site, a needle support on which a needle is mounted, the needle support being mounted so as to be able to move relative to the bearing wall between:

a pre-insertion position in which the needle is retracted with respect to the bearing wall, at least one insertion position in which the needle protrudes with respect to the bearing wall, and at least one retracted position in which the needle is once again retracted with respect to the bearing wall, a catheter mounted so as to be movable with respect to the needle and configured to dispense the product into the site, the needle support being configured to translate between the pre-insertion, the at least one insertion and the at least one retracted positions of the needle support, a pump connected to a reservoir so as to transfer the product from the reservoir to the catheter, and an electric motor configured to drive the needle support and to operate the pump to transfer the product wherein the electric motor is configured to rotate in a first direction of rotation to drive the needle support towards the at least one insertion position; and wherein the electric motor is configured to rotate in a second direction of rotation so that the pump operates to transfer the product from the reservoir to the catheter.

2. The injection device according to claim 1, wherein the electric motor is configured to drive the needle support towards the at least one retracted position when the electric motor rotates in the second direction of rotation.

3. The injection device of claim 2 wherein the injection device is configured such that when the electric motor rotates in the second direction the electric motor simultaneously drives the needle support towards the at least one retracted position and operates the pump to transfer the product from the reservoir to the catheter.

4. The injection device according to claim 1, further comprising a catheter support configured to move the catheter with the needle when the needle support changes from the pre-insertion position to the at least one insertion position and to separate the catheter from the needle so that the movement of the catheter support remains locked when the needle support changes from the at least one insertion position to the at least one retracted position.

5. The injection device according to claim 4, comprising a locking member configured to cooperate with notches carried by the catheter support to lock the movement of the catheter support and define at least first and second needle support insertion positions.

6. The injection device according to claim 4, further comprising: a drive unit, the drive unit being configured to be driven by the electric motor so that the drive unit translates the needle support; and an elastic element carried by the catheter support or a complementary drive element, the elastic element being configured to keep the complementary drive element in contact with the drive unit when the electric motor rotates in the second direction of rotation before inserting the needle.

7. The injection device according to claim 1 further comprising a base having a guide housing defining a guide axis and configured to receive the needle support, and in which the needle support comprises a blocking member configured to cooperate with a complimentary blocking member carried by the guide housing when the needle support is in the pre-insertion position and in the at least one retracted position.

8. The injection device of claim 1 comprising a drive unit, the drive unit being configured to be driven by the electric motor so that the drive unit translates the needle support.

9. An injection device for injecting a product into a site, comprising:

a body provided with a bearing wall for bearing on the site, a needle support on which a needle is mounted, the needle support being mounted so as to be able to move relative to the bearing wall between:

a pre-insertion position in which the needle is retracted with respect to the bearing wall, at least one insertion position in which the needle protrudes with respect to the bearing wall, and at least one retracted position in which the needle is once again retracted with respect to the bearing wall, a catheter mounted so as to be movable with respect to the needle and configured to dispense the product into the site, the needle support being configured to translate between the pre-insertion, the at least one insertion and the at least one retracted positions of the needle support, a pump connected to a reservoir so as to transfer the product from the reservoir to the catheter, and an electric motor configured to drive the needle support-drive unit and to operate the pump to transfer the product;

a series of teeth arranged on a circumference of a rotating element of the electric motor, the series of teeth configured to cooperate with a rack carried by a complementary drive element configured to be connected in translation with the needle support.

10. The injection device according to claim 9 further comprising a catheter support, wherein the catheter support and the complementary drive element are configured to be:

connected in translation when moving the needle support from the pre-insertion position to the at least one insertion position, and movable with respect to each other when moving the needle support from the at least one insertion position to the at least one retracted position.

11. The injection device according to claim 9, wherein the complementary drive element is configured to be connected in translation with the needle support only when moving the needle support from the pre-insertion position to the at least one insertion position, and from the at least one insertion position to the at least one retracted position, the complementary drive element being movable with respect to the needle support when the needle support is in the pre-insertion position or in the at least one retracted position.

12. The injection device of claim 9 comprising a drive unit, the drive unit being configured to be driven by the electric motor so that the drive unit translates the needle support.

13. The injection device according to claim 9, further comprising a catheter support configured to move the catheter with the needle when the needle support changes from the pre-insertion position to the at least one insertion position and to separate the catheter from the needle so that movement of the catheter support remains locked when the needle support changes from the at least one insertion position to the at least one retracted position.

14. The injection device according to claim 9 further comprising a base having a guide housing defining a guide axis and configured to receive the needle support, and in which the needle support comprises a blocking member configured to cooperate with a complimentary blocking member carried by the guide housing when the needle support is in the pre-insertion position and in the at least one retracted position.

15. An injection device for injecting a product into a site comprising:

a body provided with a bearing wall for bearing on the site, a needle support on which a needle is mounted, the needle support being mounted so as to be able to move with respect to the bearing wall between:

a pre-insertion position in which the needle is retracted with respect to the bearing wall, at least one insertion position in which the needle protrudes with respect to the bearing wall, and at least one retracted position in which the needle is once again retracted with respect to the bearing wall, a catheter configured to be movable with respect to the needle and configured to dispense the product into the site, the needle support being configured to translate between the pre-insertion, the at least one insertion and the at least one retracted positions of the needle support, a pump connected to a reservoir so as to transfer the product from the reservoir to the catheter, an-electric motor;

a rotating element having a series of teeth, the rotating element is arranged on a shaft of the electric motor:

via the rotating element, the electric motor is configured to drive the needle support and to operate the pump to transfer the product product.

16. The injection device of claim 15 comprising a drive unit, the drive unit being configured to be driven by the electric motor so that the drive unit translates the needle support.

17. The injection device according to claim 15, further comprising a catheter support configured to move the catheter with the needle when the needle support changes from the pre-insertion position to the at least one insertion position and to separate the catheter from the needle so that movement of the catheter support remains locked when the needle support changes from the at least one insertion position to the at least one retracted position.

18. The injection device according to claim 15 wherein the series of teeth are configured to cooperate with a rack carried by a complementary drive element configured to be connected in translation with the needle support.

19. The injection device according to claim 15 further comprising a base having a guide housing defining a guide axis and configured to receive the needle support, and in which the needle support comprises a blocking member configured to cooperate with a complimentary blocking member carried by the guide housing when the needle support is in the pre-insertion position and in the at least one retracted position.

* * * * *